(12) United States Patent
Buck

(10) Patent No.: US 12,303,131 B2
(45) Date of Patent: *May 20, 2025

(54) ANASTOMOTIC COUPLER

(71) Applicant: Buck Surgical, Inc., St. Louis, MO (US)

(72) Inventor: Donald W. Buck, St. Louis, MO (US)

(73) Assignee: Buck Surgical, Inc., St. Louis, MO (US)

( * ) Notice: Subject to any disclaimer, the term of this patent is extended or adjusted under 35 U.S.C. 154(b) by 927 days.

This patent is subject to a terminal disclaimer.

(21) Appl. No.: 17/365,484

(22) Filed: Jul. 1, 2021

(65) Prior Publication Data

US 2021/0346024 A1 Nov. 11, 2021

Related U.S. Application Data

(63) Continuation-in-part of application No. 17/181,440, filed on Feb. 22, 2021, now Pat. No. 11,998,208, which is a continuation of application No. 16/950,209, filed on Nov. 17, 2020, now Pat. No. 10,939,913.

(60) Provisional application No. 62/936,868, filed on Nov. 18, 2019, provisional application No. 63/061,303, filed on Aug. 5, 2020.

(51) Int. Cl.
*A61B 17/11* (2006.01)

(52) U.S. Cl.
CPC ....... *A61B 17/11* (2013.01); *A61B 2017/1107* (2013.01); *A61B 17/1114* (2013.01); *A61B 2017/1132* (2013.01); *A61B 2017/1139* (2013.01)

(58) Field of Classification Search
CPC ................. A61B 17/11; A61B 17/1114; A61B 2017/1107; A61B 2017/1132; A61B 2017/1135

See application file for complete search history.

(56) References Cited

U.S. PATENT DOCUMENTS

| | | | |
|---|---|---|---|
| 3,316,914 | A | 5/1967 | Collito |
| 3,357,432 | A | 12/1967 | Sparks |
| 6,241,743 | B1 | 6/2001 | Levin et al. |
| 6,402,767 | B1 | 6/2002 | Nash et al. |
| 6,569,173 | B1 | 5/2003 | Blatter et al. |

(Continued)

FOREIGN PATENT DOCUMENTS

| | | |
|---|---|---|
| CN | 103 750 875 A | 4/2014 |
| WO | 2009/118719 A1 | 10/2009 |
| WO | 2013/004263 A | 1/2013 |

OTHER PUBLICATIONS

International Search Report of PCT/US2020/060857 dated Jan. 18, 2021.

(Continued)

*Primary Examiner* — Todd J Scherbel
(74) *Attorney, Agent, or Firm* — POLSINELLI PC

(57) ABSTRACT

An anastomotic coupler is provided. A ring can include a plurality of receiving portions. A fixation device includes a cartridge. The cartridge includes a plurality of fasteners. The ring is aligned with the cartridge such that the receiving portions are aligned with the fasteners. Upon actuation of the fixation device, the fasteners puncture the tubular structure and are received by the receiving portions such that the tubular structure is coupled with the ring.

14 Claims, 13 Drawing Sheets

(56) References Cited

U.S. PATENT DOCUMENTS

| | | | |
|---|---|---|---|
| 10,939,913 B1* | 3/2021 | Buck | A61B 17/1155 |
| 11,672,539 B2 | 6/2023 | Agarwal et al. | |
| 11,998,208 B2* | 6/2024 | Buck | A61B 17/11 |
| 2001/0039425 A1* | 11/2001 | Dakov | A61B 17/11 |
| | | | 606/153 |
| 2002/0082625 A1 | 6/2002 | Huxel et al. | |
| 2004/0054405 A1 | 3/2004 | Richard et al. | |
| 2006/0004394 A1 | 1/2006 | Amarant | |
| 2008/0114385 A1 | 5/2008 | Byrum et al. | |
| 2008/0200938 A1 | 8/2008 | Lui | |
| 2011/0106118 A1 | 5/2011 | Son et al. | |
| 2011/0270287 A1* | 11/2011 | Borghi | A61B 17/11 |
| | | | 606/153 |
| 2011/0306994 A1 | 12/2011 | Bassan et al. | |
| 2013/0110140 A1 | 5/2013 | Lin et al. | |
| 2013/0193190 A1 | 8/2013 | Carter et al. | |
| 2013/0267968 A1 | 10/2013 | Ferlin | |
| 2019/0150928 A1 | 5/2019 | Boiman et al. | |
| 2019/0175172 A1 | 6/2019 | Kollar et al. | |
| 2019/0321046 A1 | 10/2019 | Williams | |
| 2020/0113567 A1 | 4/2020 | Bakos et al. | |
| 2020/0337707 A1 | 10/2020 | Ad-El et al. | |
| 2023/0009775 A1 | 1/2023 | Buck | |
| 2023/0240681 A1 | 8/2023 | Higdon et al. | |

OTHER PUBLICATIONS

International Preliminary Report on Patentability of PCT/US20/60857 dated Feb. 9, 2021.

European Search Report (EESR) of European Patent Application No. EP 20890827.7, dated Jul. 24, 2023.

Vocabulary.com definition for "needle" accessed Oct. 20, 2023; (4 Pages) https://www.vocabulary.com/dictionary/needle.

Vocabular.com definiton for "pin" accessed Oct. 20, 2023; (4 Pages) https://www.vocabulary.com/dictionary/pin.

English Translation of Office Action for Brazil Application No. 112022004182.9, issued Nov. 8, 2022 (4 Pages).

Office Action for U.S. Appl. No. 17/181,440, issued Oct. 26, 2023 (28 Pages).

Office Action for Chinese Application No. 202080069581.8, issued on May 8, 2023, 08 Pages (5 Pages of Official Copy and 3 Pages of English Translation).

International Search Report (ISR of PCT/US2024/050874, dated Dec. 12, 2024.

International Search Report (ISR) of PCT/US2024/053172, dated Jan. 8, 2024.

Office Action for U.S. Appl. No. 17/536,439, dated Jan. 21, 2025 (8 pages).

* cited by examiner

ANASTOMOTIC COUPLER

CROSS-REFERENCE TO RELATED APPLICATIONS

This application is continuation-in-part application of U.S. application Ser. No. 17/181,440 filed Feb. 22, 2021, which is a continuation application of U.S. application Ser. No. 16/950,209 filed Nov. 17, 2020, now U.S. Pat. No. 10,939,913, which claims the benefit of U.S. Provisional Patent Application No. 62/936,868, filed in the U.S. Patent and Trademark Office on Nov. 18, 2019, and U.S. Provisional Patent Application No. 63/061,303, filed in the U.S. Patent and Trademark Office on Aug. 5, 2020, each of which is incorporated herein by reference in its entirety for all purposes.

FIELD

The present disclosure relates generally to an anastomotic coupler. In at least one example, the present disclosure relates to a surgical system and method to utilize an anastomotic coupler to connect two tubular structures such as vessels, esophagus, intestine, lymphatic structure, and/or graft material.

BACKGROUND

An anastomosis is a connection between two luminal structures. Commonly, these connections can occur with blood vessels (for example, vascular anastomosis), or tubular gastrointestinal structures (for example, intestines, stomach, esophagus). Conventional techniques allow the anastomosis to be completed between two ends (referred to as end-to-end anastomosis), or between the end of one structure and the side of another structure (referred to as end-to-side anastomosis). Procedures requiring these anastomoses are carried out thousands of times per day, globally. Likewise, multiple surgical specialties rely upon the creation of reliable, unobstructed anastomoses for successful treatment of their respective patients.

BRIEF DESCRIPTION OF THE DRAWINGS

Implementations of the present technology will now be described, by way of example only, with reference to the attached figures, wherein.

DETAILED DESCRIPTION

Figure 1:
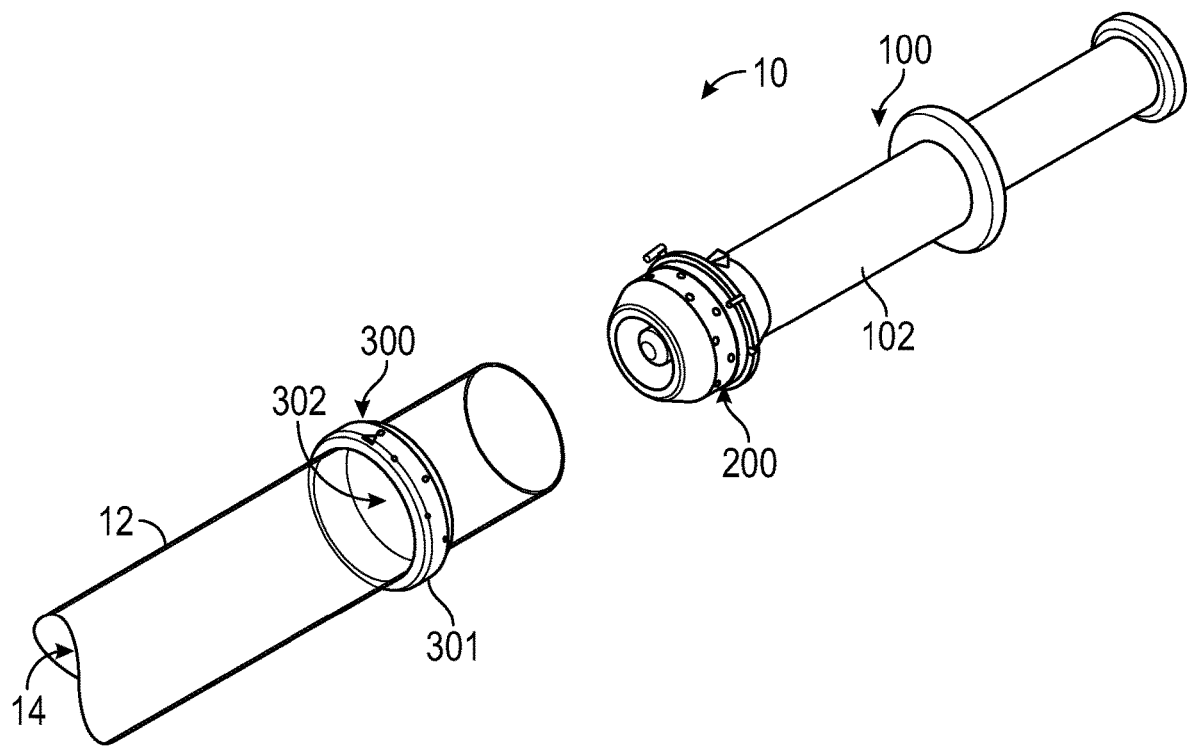
FIG. 1 illustrates a diagram of an anastomotic coupler.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the examples described herein. The drawings are not necessarily to scale and the proportions of certain parts may be exaggerated to better illustrate details and features of the present disclosure.

The original technique for vascular suture anastomoses was created by Alexis Carrel between 1901-1910. This pioneering work resulted in Carrel receiving the Nobel Prize in 1912. Despite 100 years of surgical evolution and innovation since that discovery, the majority of vascular anastomoses to this day still employ suture techniques similar to Carrel's initial description in the early 1900s. In the 1970s, gastrointestinal stapling devices were introduced, which quickly replaced primary suture techniques for bowel anastomoses. However, most surgeons still employ circumferential suture techniques in the serosal layer overlying the stapled anastomosis for added support. Although generally successful, these techniques can take long periods of time, often require additional surgical expertise, and if not performed correctly, may result in leakage (blood, stool contents, gastric contents, lymphatic fluid), constriction, stenosis, and/or obstruction at the anastomotic site. In the case of vascular anastomoses, stenosis and/or obstruction can result in catastrophic complications such as heart attack, stroke, peripheral limb ischemia, amputation, death, and reconstructive failure and soft-tissue loss. For example, in the setting of gastrointestinal anastomoses, these complications can result in extra-luminal leak of gastrointestinal contents, infection, sepsis, obstruction, and death.

With the understood importance of reliable, open anastomoses, alternatives to sutures and staples have been used. An example of a vascular anastomotic coupler is described, for instance, in U.S. Patent Pub. No. 2015/0088172 A1 (the '172 Publication). This coupler has two circular ends with spikes or pins. The vessel is brought through the ring and the vessel wall is everted, or rolled over, the pins for securement as shown in FIGS. 2A and 2B of the '172 Publication. This is completed on each vessel end, and the two rings are then brought together with the spikes/pins being forced into the opposite ring to join the ends together as shown in FIG. 1C of the '172 Publication. However, because of the potential for micro-motion of the vessels and size mismatch due to the anastomotic coupler of the '172 Publication, blood leakage may happen, and/or one of the pins may tear through the vessel wall creating a leak and/or site for platelet aggregation and thrombosis (blood clot formation). Likewise, with the anastomotic coupler of the '172 Publication, for thicker walled, less elastic vessels, particularly arteries, everting vessel edges can be quite difficult and may result in trauma to the vessel wall (intima) and/or stenosis at the anastomosis, both of which can create platelet aggregation, turbid flow, and/or thrombosis with subsequent obstruction of flow. Additionally, the technique of the '172 Publication requires additional specialized equipment (surgical microscope, high-powered loupe magnification) to use. For gastrointestinal stapled anastomoses, many procedures are performed either side-to-side which is not a natural pathway for intestinal smooth muscle propulsion of stool contents (for example, non-longitudinal flow along the length of the intestine), or end-to-end, which requires a separate, remote full-thickness bowel access incision for deployment, thereby creating a secondary weak point for potential leak, or adhesion formation.

Referring now to FIG. 1, an anastomotic coupler 10 is provided. The anastomotic coupler 10 is provided to create a connection between adjacent tubular structures 12. The tubular structure 12 can include blood vessels, grafts, prostheses, gastrointestinal structures, esophagus, lymphatics, and/or any other suitable channels of the body or the operation for which the tubular structure 12 is created. The tubular structure 12 forms a lumen 14 through which matter can be passed, for example blood, food, fluids, and/or cells.

The anastomotic coupler 10 includes a ring 300 forming an aperture 302. The ring 300 is operable to receive a tubular structure 12 through the aperture 302. While the ring 300 as illustrated in FIG. 1 has a substantially circular shape, the ring 300 can have any suitable shape such as rectangular, triangular, octagonal, hexagonal, and/or oval. Additionally, the ring 300 as illustrated in FIG. 1 is a singular solid piece, in some examples, for ease of application or manufacturing purposes, the ring 300 can include two semi-circular or arc-type pieces that are joined together around the tubular structure 12.

The size of the lumen 302 of the ring 300 can vary based on the application and the size of the tubular structure 12. For example, the diameter of the lumen 302 can range from about 0.5 millimeters (mm) (for example for lymphatic connections) to about 60 millimeters (for example for gastrointestinal connections). Due to the range of diameters for the ring 300, and the range of diameters for the tubular structure 12, the appropriate ring 300 can be selected by measuring the internal diameter of the tubular structure 12. This can be accomplished, for example, with an intraluminal measurement guide/device. If there is a significant size mismatch (1 mm or greater) between the tubular structure 12 and the ring 300, then a short, cylindrical tube connector with a corresponding male and female end can be used to allow for gradual transition in size in any direction to accommodate the size difference. For example, a cylindric tube can be provided that tapers in size such that one end is 1 mm-2 mm larger/smaller than the other end, which would enable a connection of a 1 mm vessel to a 2.5 mm-3.5 mm vessel during microsurgical procedures without problem and vice versa.

Figure 2:
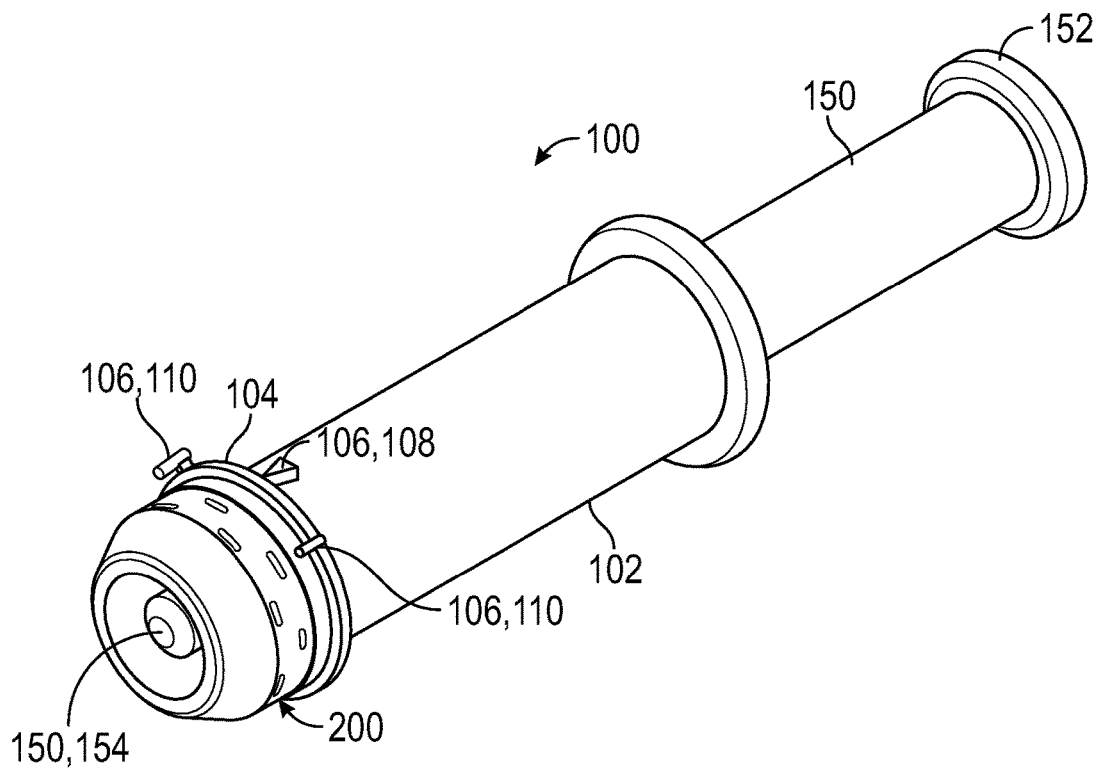
FIG. 2 illustrates a fixation device.

Referring also to FIG. 2, the anastomotic coupler 10 also includes a fixation device 100. The fixation device 100 is operable to couple the tubular structure 12 with the ring 300. The fixation device 100 can include a housing 102 and a cartridge 200. The cartridge 200 includes a plurality of fasteners 206 (as shown in FIGS. 5-10B). The fasteners 206 are operable to puncture the tubular structure 12 and be partially received in the ring 300 to couple the tubular structure 12 with the ring 300. In at least one example, the cartridge 200 can be removably coupled with the housing 102. Accordingly, the cartridge 200 may be replaceable to allow multiple uses of the fixation device 100. In some examples, the cartridge 200 may not be removable such that the fixation device 100 is provided for a one-time use. The fixation device 100 can include a pusher rod 150 operable to actuate the fixation device 100 to drive the fasteners 206 from the cartridge 200. Upon actuation of the fixation device 100, the pusher rod 150 can translate along a longitudinal axis.

Figure 3:
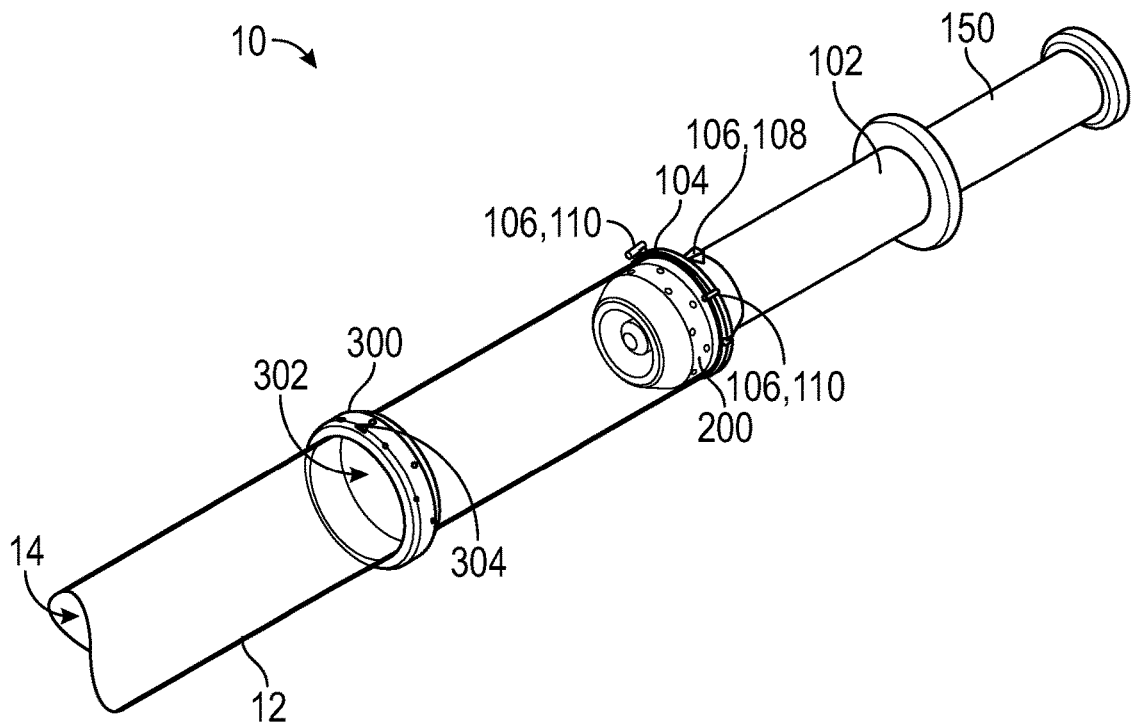
FIG. 3 illustrates a tubular structure being received by a fixation device.

The fixation device 100 includes stop 104 to receive the tubular structure 12. In at least one example, the stop 104 can be formed as a portion of the cartridge 200 to ensure alignment with the cartridge 200. In some examples, the stop 104 can be formed as a portion of the housing 102. The stop 104 extends radially from the housing 104 such that a free end of the tubular structure abuts the stop 104. As illustrated in FIG. 3, the housing 102 receives the free end of the tubular structure 12 such that the cartridge 200 is inserted into the lumen 14 of the tubular structure. When correctly positioned, the free end of the tubular structure 12 abuts the stop 104. The stop 104 ensures the placement and alignment of the ring 300, the cartridge 200, and the free end of the tubular structure 12. The alignment of the ring 300, the cartridge 200, and the free end of the tubular structure 12 is critical to ensure adequate connection between the tubular structure 12 and another tubular structure 12.

Figure 4:
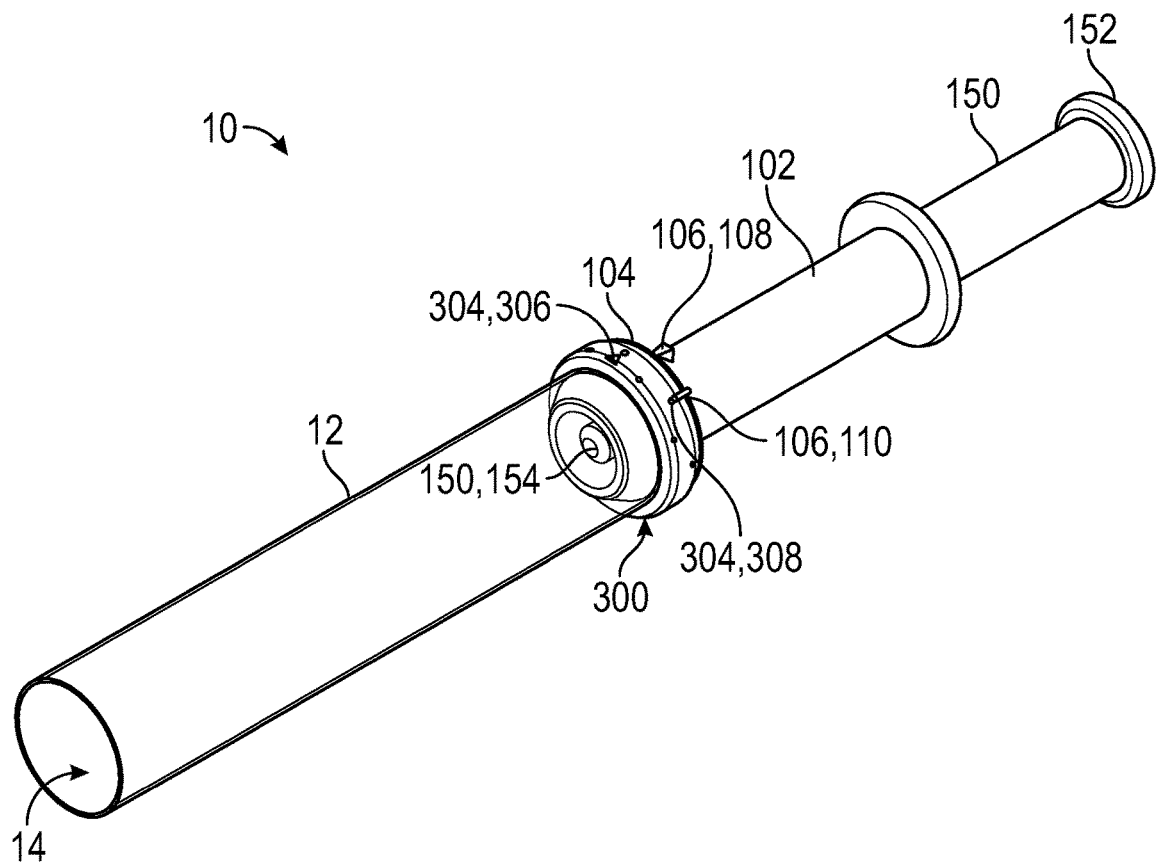
FIG. 4 illustrates a ring being aligned with a cartridge of the fixation device.

As illustrated in FIG. 4, after the tubular structure 12 is received by the fixation device 100 and abuts the stop 104, the ring 300 can be positioned to abut the stop such that the ring 300 is aligned with the free end of the tubular structure 12.

The stop 104 can include a plurality of alignment components 106 which correspond with alignment components 304 of the ring 300. Accordingly, when the ring 300 is aligned and/or correctly positioned, the alignment components 106 of the stop 104 are aligned with the alignment components 304 of the ring 300. In some examples, the alignment components 106, 304 can include one or more alignment markers 108, 304. The alignment markers 108, 304 can be shaped, for example as triangles. Accordingly, to align the ring 300, the tips of the triangles for the alignment markers 108, 304 can point towards one another. In some examples, the alignment components 106, 304 can include one or more alignment pins 110 and corresponding alignment receivers 308. When the ring 300 is aligned, the alignment pins 100 can be received by the alignment receivers 308. While the figures illustrate the alignment pins 100 being disposed on the fixation device 100 and the alignment receivers 308 being disposed on the ring 300, in some examples, the alignment pins 100 may be disposed on the ring 300 and the alignment receivers can be disposed on the fixation device 100.

Figure 5:
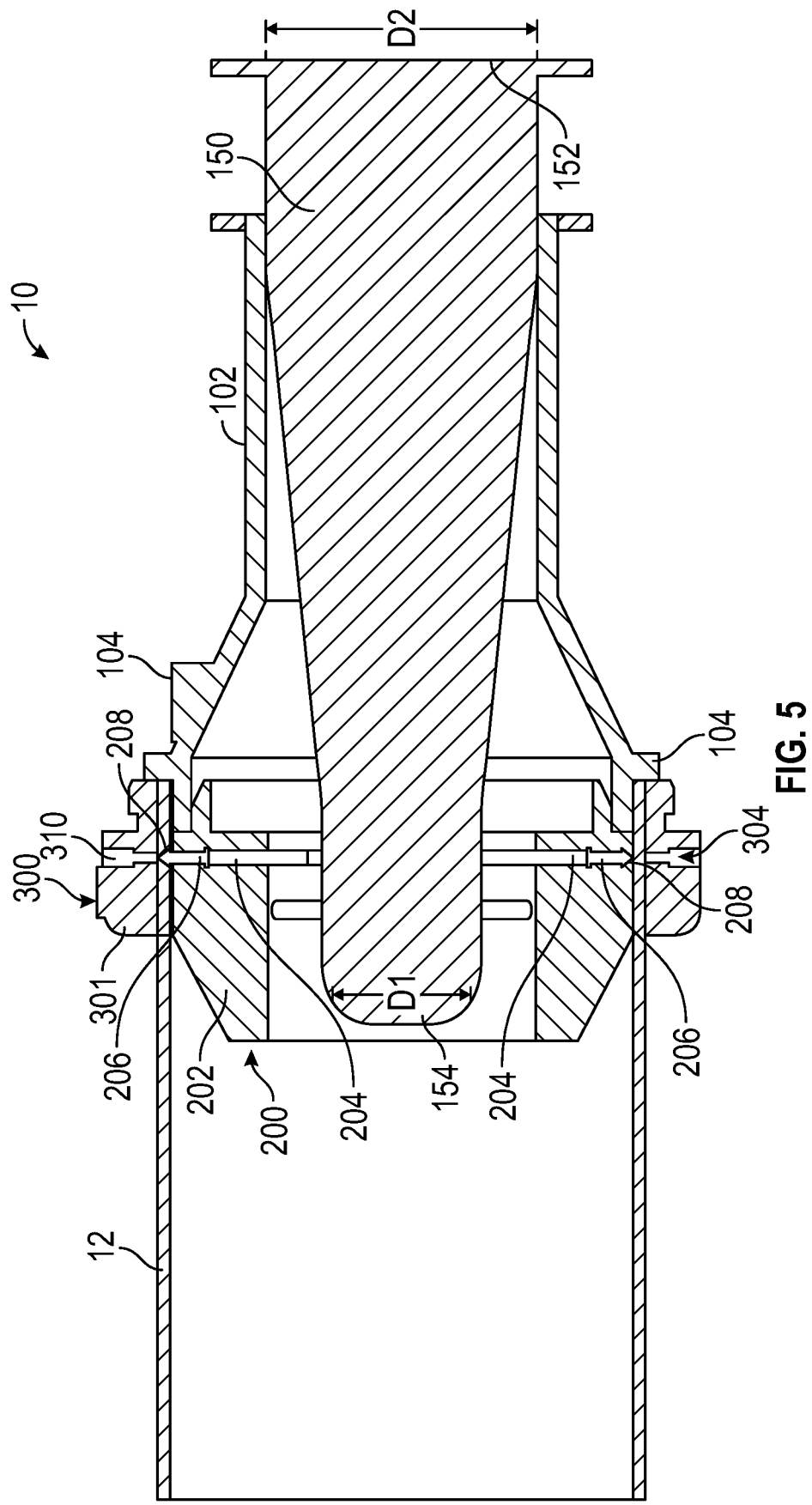
FIG. 5 illustrates a cross-sectional view of FIG. 4.

FIG. 5 illustrates a cross-sectional view of the tubular structure 12, the ring 300, and the cartridge 200 aligned. In addition to ensuring the ring 300 aligns with the free end of the tubular structure 12, the ring 300 is aligned with the cartridge 200. When the ring 300 is properly aligned with the cartridge 200, a plurality of receiving portions 310 of the ring 300 are aligned with the plurality of fasteners 206 of the cartridge 200.

The fasteners 206 can be any suitable fastener 206 to couple the ring 300 with the tubular structure 12 and prevent movement between the ring 300 and the tubular structure 12. For example, the fasteners 206 can include tacks 600, 700 (as shown in FIGS. 6 and 7), staples 800 (as shown in FIG. 8), pins, adhesive, internal ring, internal mesh, wire, clamp, coil, stent, and/or suture.

Figure 6:
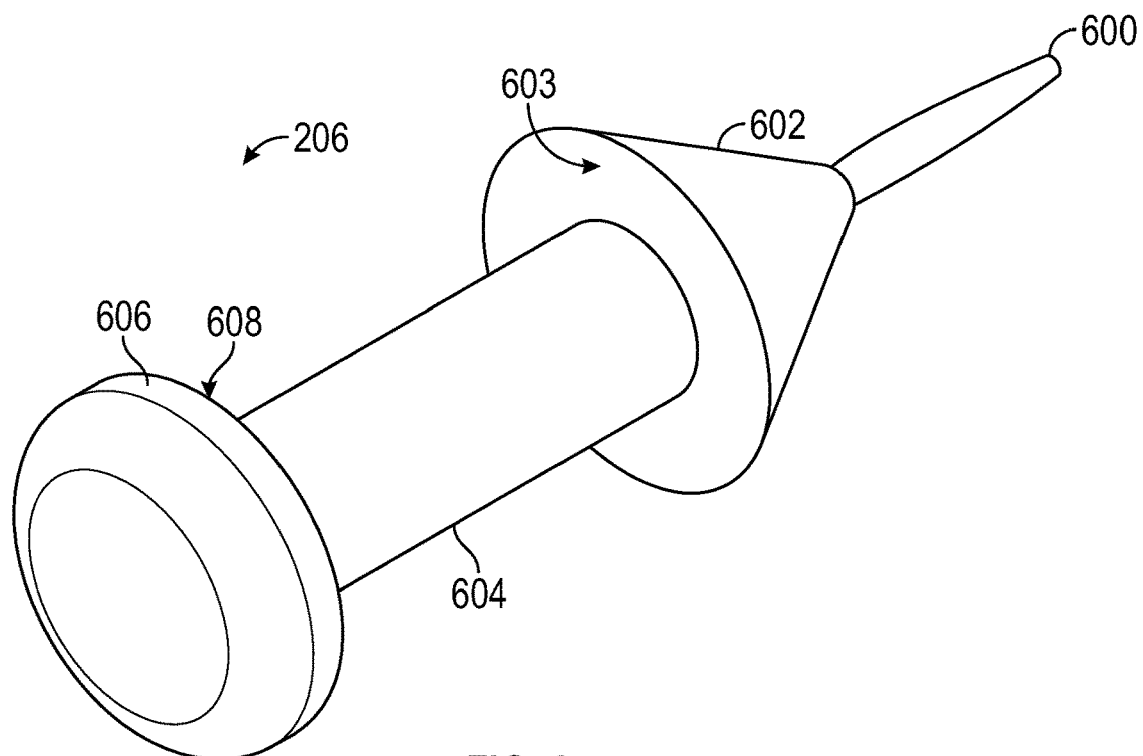
FIG. 6 illustrates an exemplary fastener.

As illustrated in FIG. 6, the tack 600 can include a puncturing portion 602 which is operable to puncture the tubular structure 12. An abutment surface 603 abuts against a surface of the corresponding receiving portion 310 of the ring 300. A body 604 spans the thickness of the wall of the tubular structure 12, and an end 606 includes an abutment surface 608 which abuts against the inner surface of the tubular structure 12. The abutment surfaces 603, 608 prevent the fastener 206 from being removed from the tubular structure 12 and the ring 300.

Figure 7:
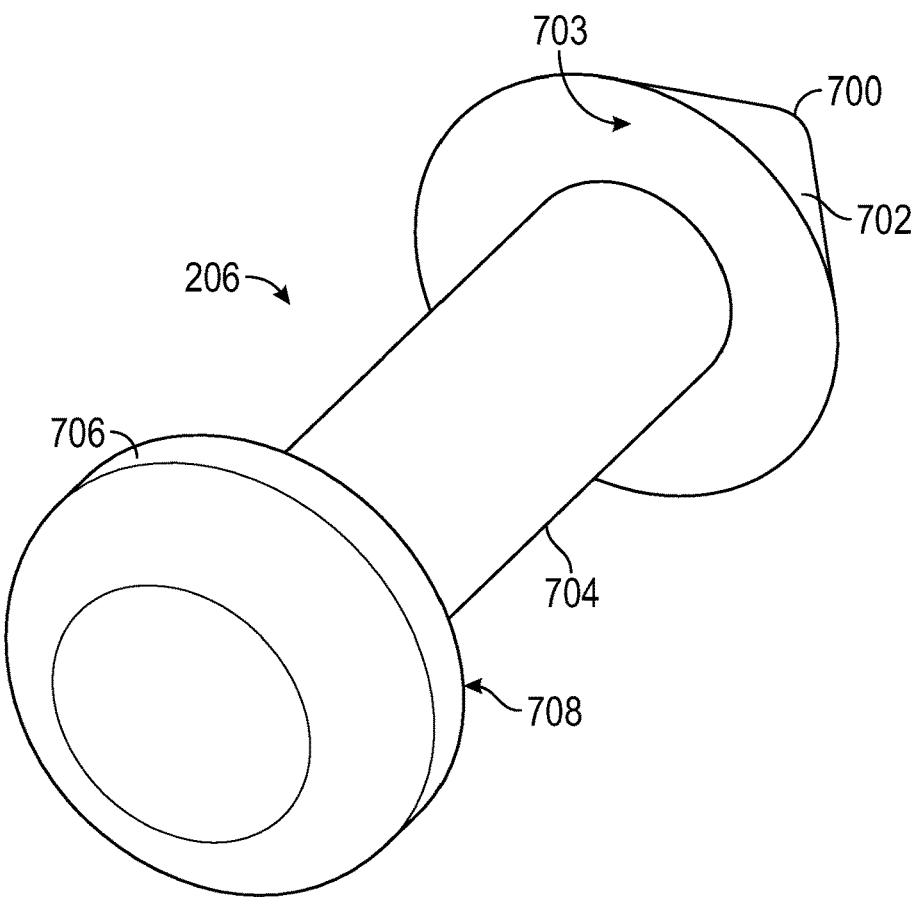
FIG. 7 illustrates another example of a fastener.

As illustrated in FIG. 7, the tack 700 can include a puncturing portion 702 which is operable to puncture the tubular structure 12. The exemplary tack 700 does not include as long of a puncturing portion 702 as the puncturing portion 602 as illustrated in FIG. 6. An abutment surface 703 abuts against a surface of the corresponding receiving portion 310 of the ring 300. A body 704 spans the thickness of the wall of the tubular structure 12, and an end 706 includes an abutment surface 708 which abuts against the inner surface of the tubular structure 12. The abutment surfaces 703, 708 prevent the fastener 206 from being removed from the tubular structure 12 and the ring 300.

Figure 8:
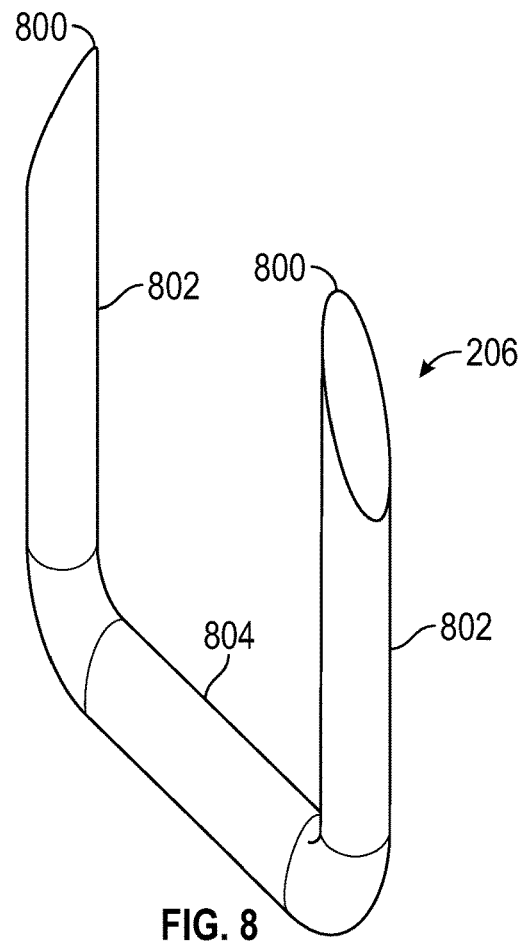
FIG. 8 illustrates another example of a fastener.

As illustrated in FIG. 8, the staple 800 can include two puncturing portions 802 which are operable to puncture through the tubular structure 12 and be received in the corresponding receiving portion 310 of the ring 300. A body 804 spans between the puncturing portions 802 and is operable to abut the inner surface of the tubular structure 12 to prevent the fastener 206 from being removed from the tubular structure 12. In at least one example, the puncturing portions 802 may be operable to bend or deform when received in the receiving portion 310 to prevent the puncturing portions 802 from being removed from the ring 300, ensuring coupling of the tubular structure 12 with the ring 300.

Figure 9:
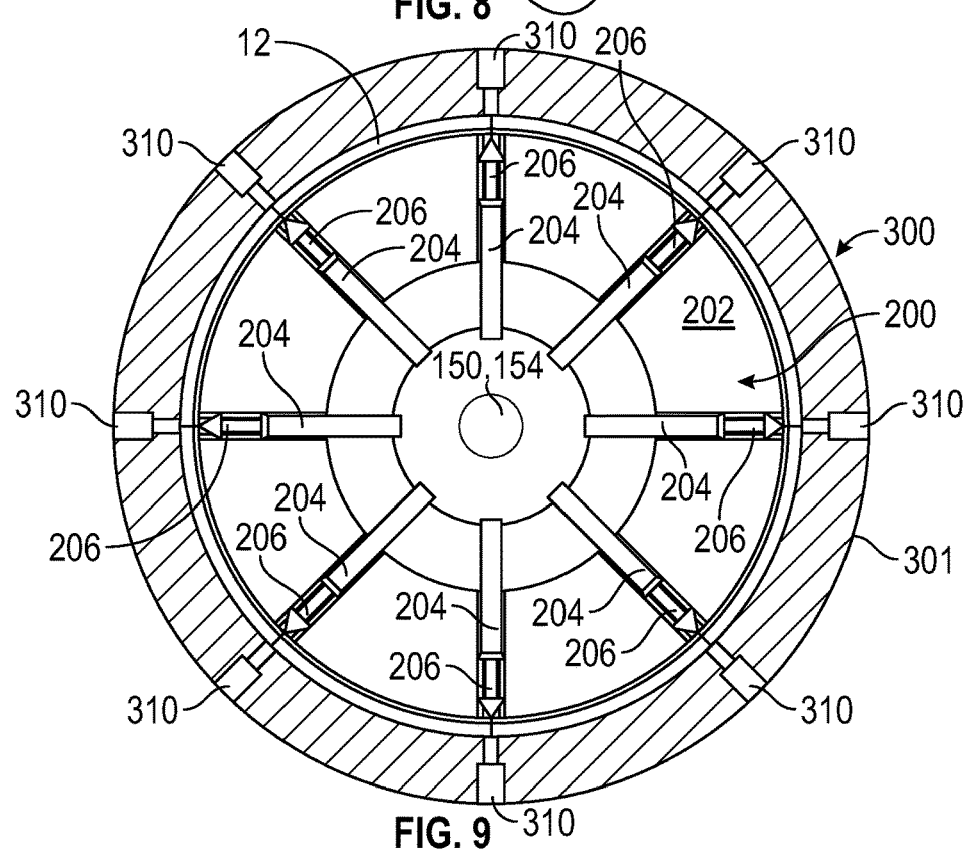
FIG. 9 illustrates a cross-sectional view of the cartridge aligned with the ring.

Referring to FIGS. 5 and 9, the cartridge 200 can include a plurality of drivers 204 corresponding with the plurality of fasteners 206. Upon actuation of the fixation device 100, the drivers 204 activate to push the corresponding fasteners 206 radially outward from the cartridge 200. The drivers 204 may include rods which abut the fasteners 206 and towards the center of the body 202 of the cartridge 200. In some examples, the drivers 204 may be spring loaded.

The pusher rod 150, as illustrated in FIG. 5, is tapered from a front portion 154 with a smaller diameter D1 to a rear portion 152 with a larger diameter D2 which is greater than the smaller diameter D1. The drivers 204 may abut the fasteners 206 on one end while extending into the cartridge 200 so that the opposing end of the fasteners 206 abut the pusher rod 150.

Figure 10A:
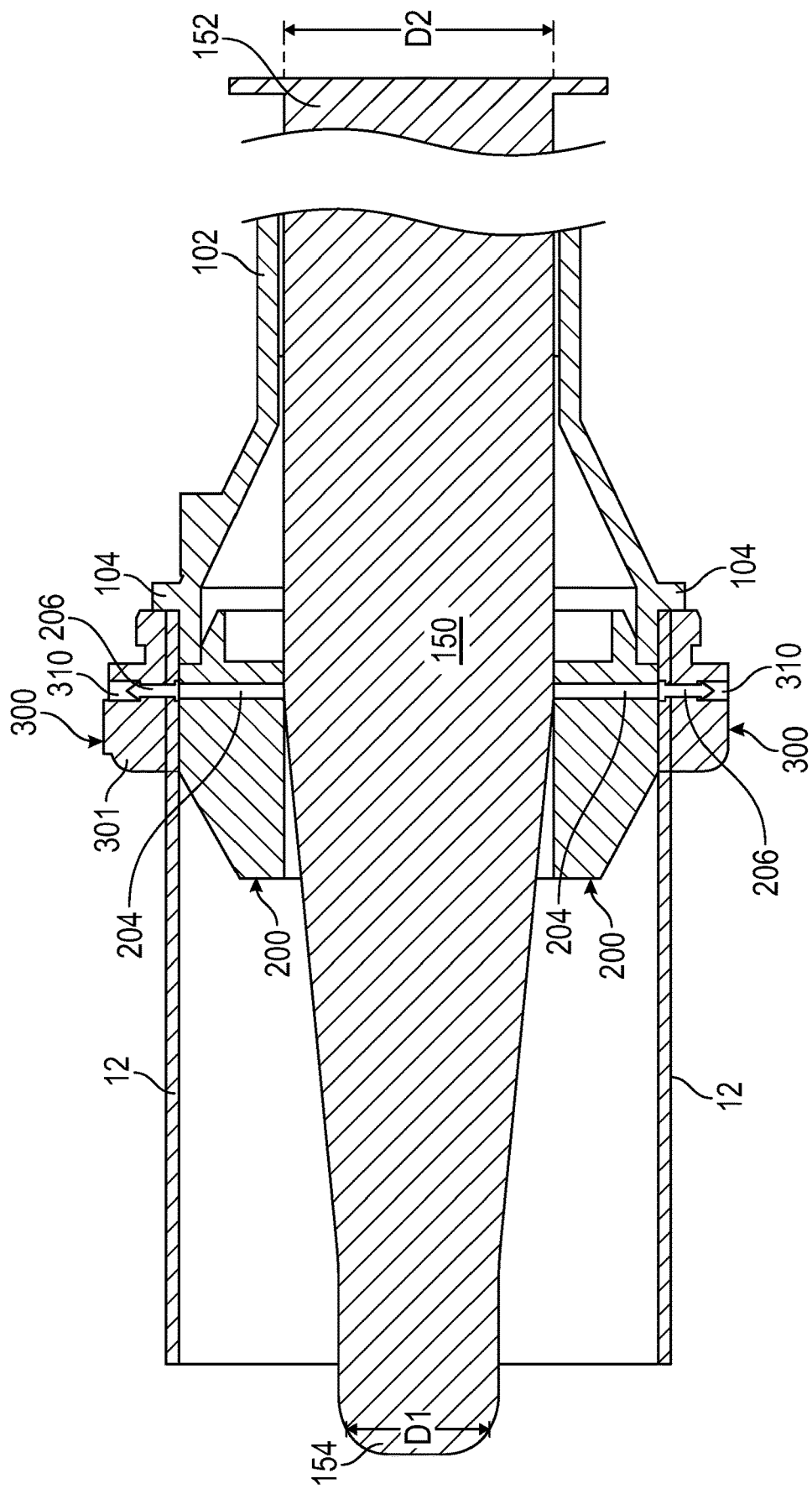
FIG. 10A illustrates actuation of the fixation device.
Figure 10B:
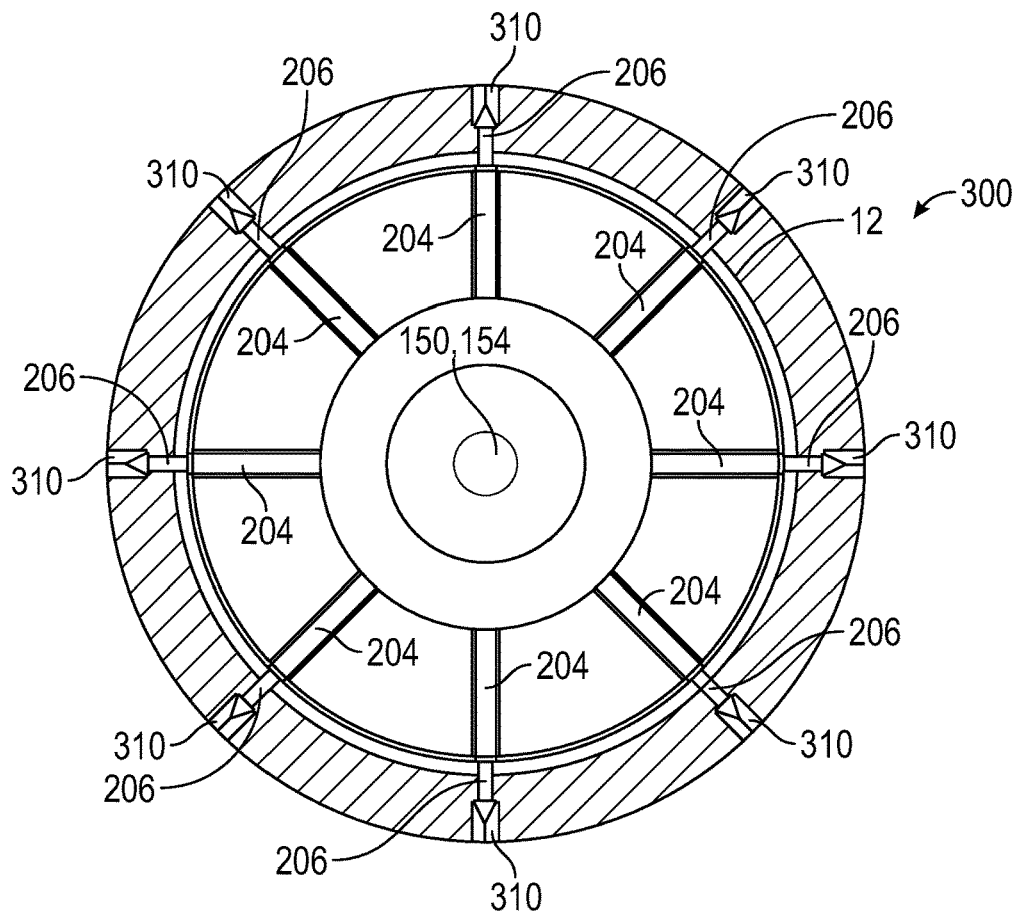
FIG. 10B illustrates a cross-sectional view of FIG. 10A.

Referring to FIGS. 10A and 10B, the fixation device 100 is actuated. Actuation of the fixation device 100 can include translating the pusher rod 150 along the longitudinal axis through the cartridge 200 from the front portion 154 towards the rear portion 152. The pusher rod 150, increasing in thickness, then activates the drivers 204 to drive the fasteners 206 radially outward from the cartridge 200, through the tubular structure 12, and into the receiving portions 310 of the ring 300. Once the ring 300 is coupled with the tubular structure 12, the fixation device 100 can be removed from the tubular structure 12. The ring 300 is then affixed or secured to the end of the tubular structure 12, maintaining the structure of the lumen of the tubular structure 12.

The fixation device 100, the ring 300, and/or the fasteners 206 can be made from mechanically suitable materials that are approved, and have sufficient strength, for use in the human or animal body. For example, the following materials, alone or in any combination, can be used: metals, in particular titanium or stainless steel, including the special alloys used for implants and medical instruments, nitinol, carbon materials, including carbon fiber meshes, soft plastic, for example silicone, hard plastic, for example Teflon, ceramic material, and/or bioresorbable material. The fixation device 100, the ring 300, and/or the fasteners 206 can be provided entirely or partially with a coating and/or structure that prevents or at least reduces the adherence of blood constituents. Such a coating can be composed of a material that smooths the surface. In at least one example, the coating can also contain anti-thrombotic medicaments (e.g. heparin).

Figure 11:
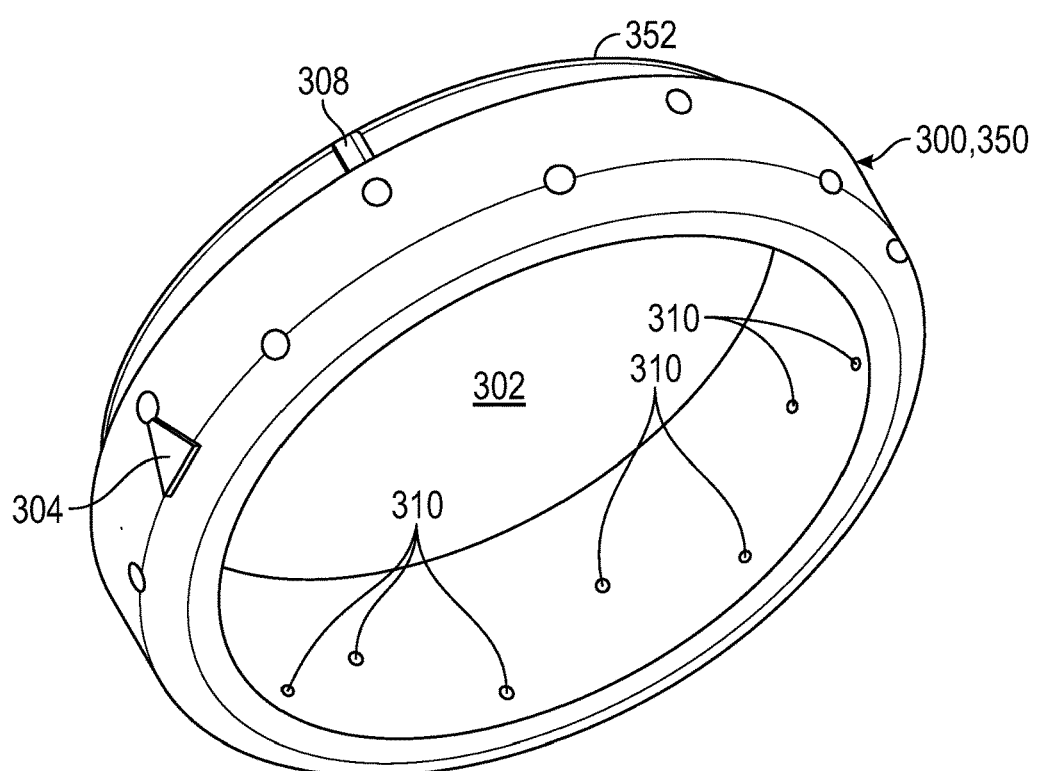
FIG. 11 illustrates an exemplary ring.
Figure 12:
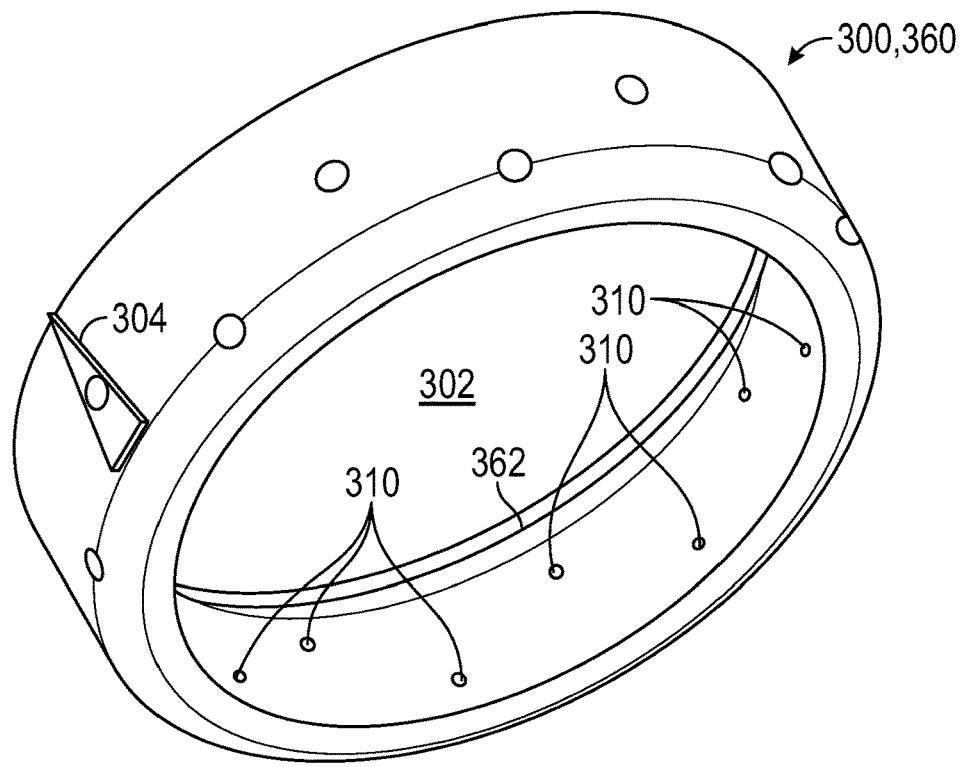
FIG. 12 illustrates an example of another ring.

The above process of coupling the ring 300 with the tubular structure 12 can be repeated for a second tubular structure 12 with a second ring 300. For example, FIG. 11 illustrates an exemplary male ring 350, and FIG. 12 illustrates an exemplary corresponding female ring 350. Similar to the ring 300 discussed above, the male ring 350 and the female ring 360 each include an aperture 302 operable to receive a tubular structure 12, receiving portions 310 operable to receive the fasteners 206, and alignment portions 304, 308. The male ring 350 includes a mating portion 352, and the female ring 360 includes a corresponding mating portion 362. The mating portion 352 is operable to couple with the mating portion 362 to couple the male ring 350 and the female ring 360 with one another. As illustrated in FIGS. 11 and 12, the mating portion 352 of the male ring 350 extends from the ring 350 and is operable to be received by the mating portion 362 of the female ring 360. In some examples, the rings 300 can be coupled with one another by, for example, fastening, snapping, clamping, stenting, tacking, pinning, loop and hook, adhesive, and/or other connecting method so long as the rings 300 are securely coupled with one another.

Figure 13:
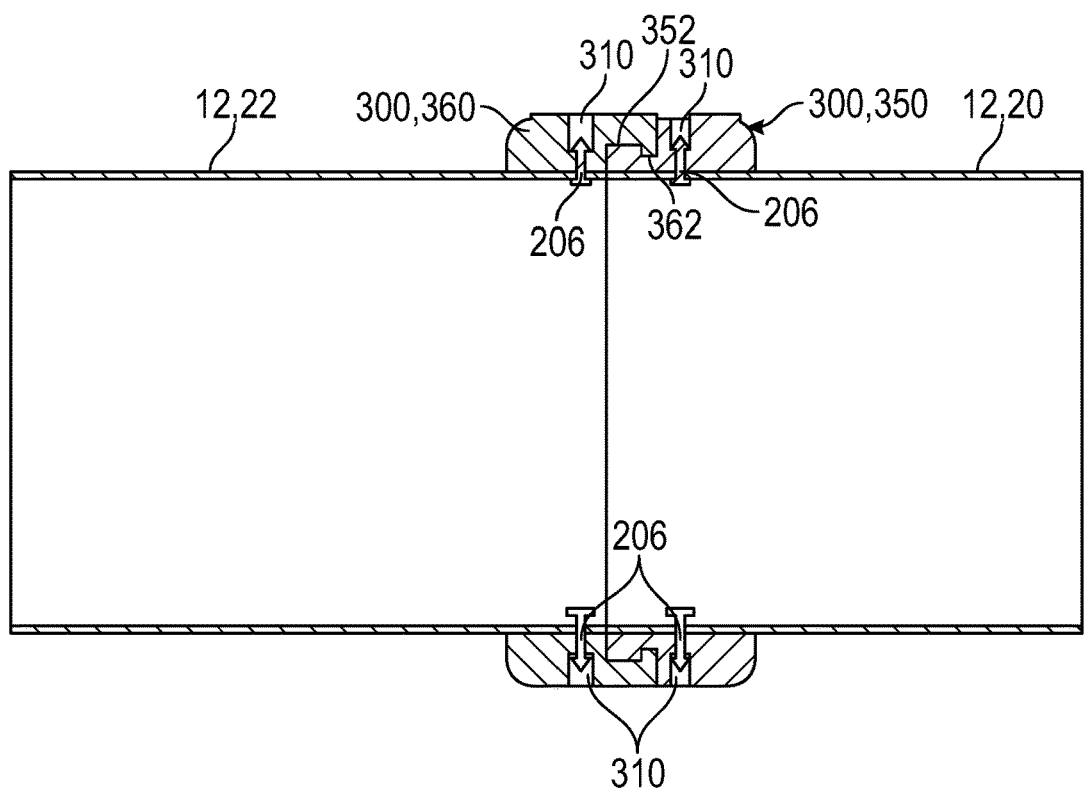
FIG. 13 illustrates a cross-sectional view of two rings coupled with one another to join two tubular structures.

As illustrated in FIG. 13, when the rings 350, 360 are coupled with one another, the lumens 14 of the two tubular structures 20, 22 are aligned in fluid communication with one another. In at least one example, the rings 350, 360 can create a seal to prevent fluid leakage. Accordingly, the anastomotic coupler 10 provides a more reliable, faster, more secure anastomotic coupling device to create a sealed, leak-proof, open connection between the ends of the tubular structures 20, 22 and allow for "stented" unobstructed flow of luminal contents through the connection/anastomosis (e.g. blood, lymph, fluid, stool contents, gastric contents, etc.). This connection can be strong enough to withstand tension, traction, and high flow pressure, which may occur with distal obstruction.

Figure 14:
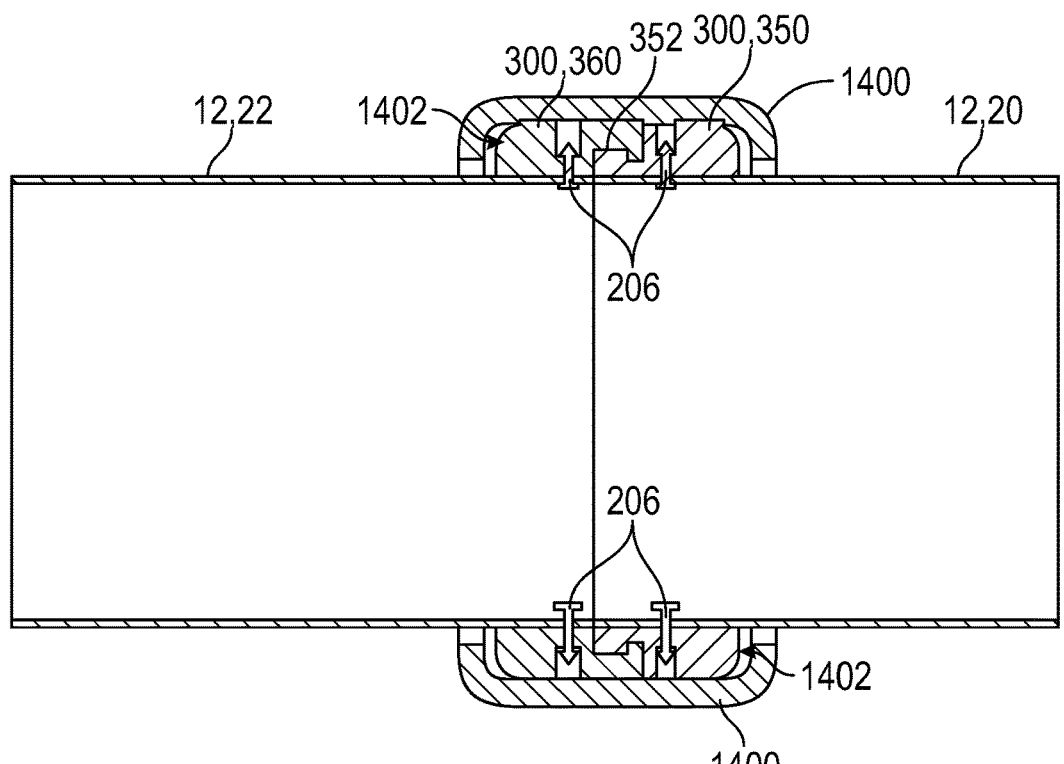
FIG. 14 illustrates a cap disposed over the two rings of FIG. 13.
Figure 15:
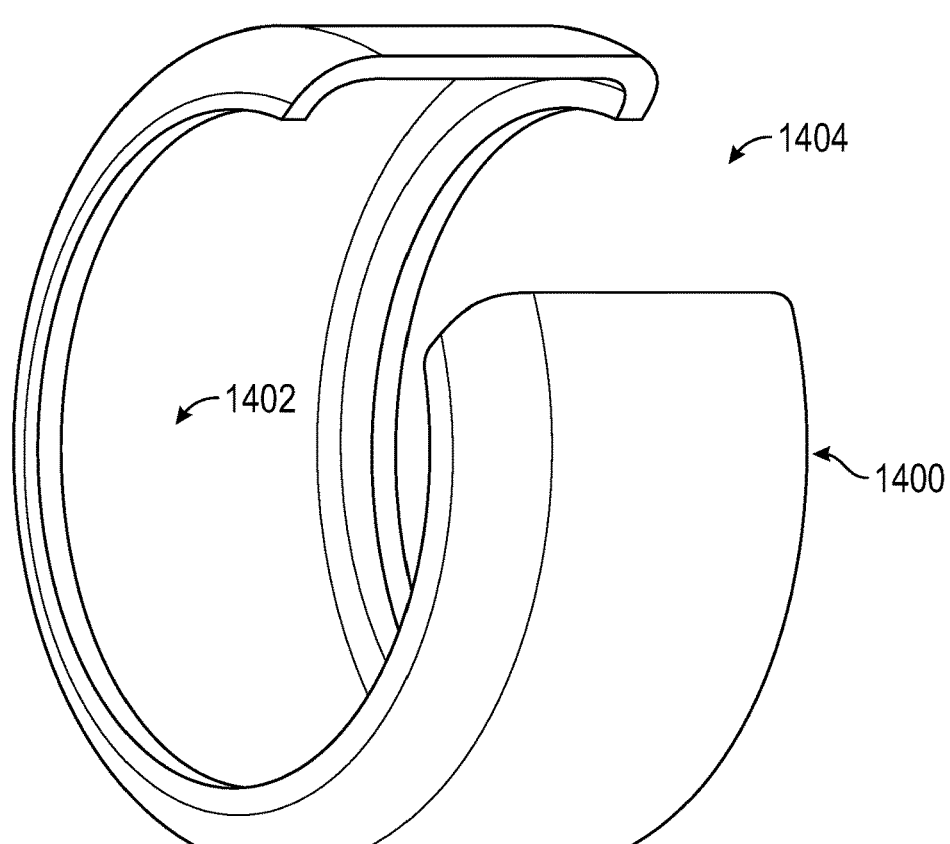
FIG. 15 illustrates an exemplary cap.

As illustrated in FIG. 14, a cap 1400 can be provided over the two rings 350, 360. The cap 1400 can assist in ensuring the connection between the rings 350, 360, as well as protecting the rings 350, 360 from external damage. As illustrated in FIG. 15, the cap 1400 can include a recess 1402 which is operable to receive the two rings 350, 360. An opening 1404 can be formed such that the cap 1400 can be deformed to snap over the two rings 350, 360.

Figure 16:
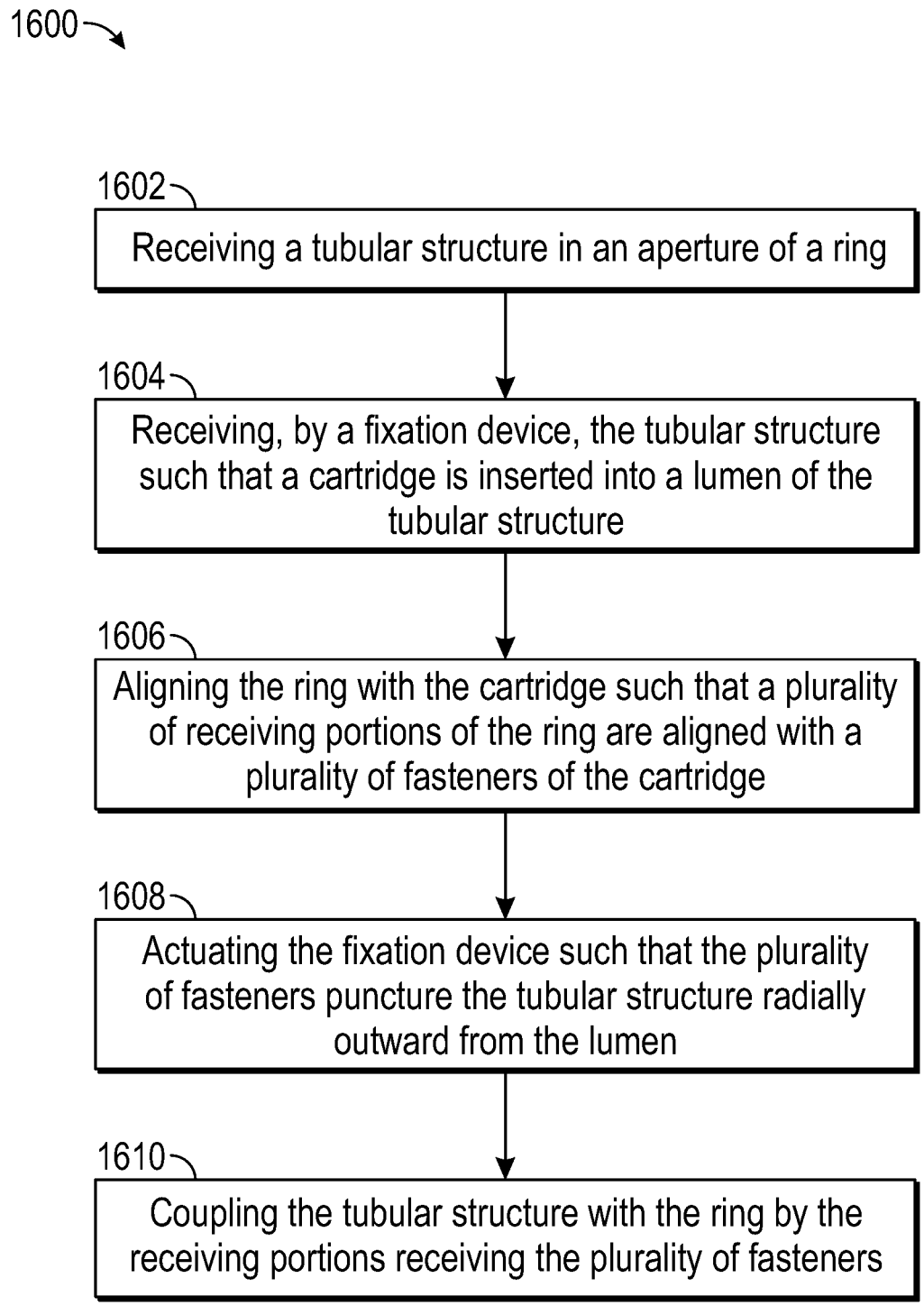
FIG. 16 is a flow chart of a method for utilizing an anastomotic coupler.

Referring to FIG. 16, a flowchart is presented in accordance with an example embodiment. The method 1600 is provided by way of example, as there are a variety of ways to carry out the method. The method 1600 described below can be carried out using the configurations illustrated in FIG. 1-15, for example, and various elements of these figures are referenced in explaining example method 1600. Each block shown in FIG. 16 represents one or more processes, methods or subroutines, carried out in the example method 600. Furthermore, the illustrated order of blocks is illustrative only and the order of the blocks can change according to the present disclosure. Additional blocks may be added or fewer blocks may be utilized, without departing from this disclosure. The example method 1600 can begin at block 1602.

At block 1602, a first tubular structure is received in an aperture of a first ring.

At block 1604, a fixation device receives the first tubular structure such that a first cartridge is inserted into a lumen of the first tubular structure.

At block 1606, the first ring is aligned with the first cartridge such that a plurality of receiving portions of the first ring are aligned with a plurality of fasteners of the first cartridge.

At block 1608, the fixation device is actuated such that the plurality of fasteners puncture the first tubular structure radially outward from the lumen. The cartridge can include a plurality of drivers corresponding with the plurality of fasteners. Upon actuation of the fixation device, the drivers activate to push the corresponding fasteners radially outward from the cartridge. In at least one example, the fixation device can include a pusher rod. The pusher rod can be tapered from a front portion with a smaller diameter to rear portion with a larger diameter. Upon actuation of the fixation device, the pusher rod can translate along a longitudinal axis to activate the drivers. In at least one example, to activate the drivers, the pusher rod translates along the longitudinal axis and passes through the cartridge from the front portion to the rear portion such that the pusher rod abuts and pushes the drivers and the corresponding fasteners radially outward from the cartridge.

At block 1610, the first tubular structure is coupled with the first ring by the receiving portions receiving the plurality of fasteners.

In at least one example, a second tubular structure can be received in an aperture of a second ring. A fixation device can receive the second tubular structure such that a second cartridge is inserted into a lumen of the second tubular structure. In at least one example, the fixation device may be the same fixation device that was utilized for the first ring. In some examples, the fixation device may be the same fixation device utilized for the first ring with a second cartridge that replaced the first cartridge. In some examples, the fixation device may be a second fixation device. The second ring can be aligned with the second cartridge such that a plurality of receiving portions of the second ring are aligned with a plurality of fasteners of the second cartridge. The fixation device can be actuated such that the plurality of fasteners puncture the second tubular structure radially outward from the lumen. The second tubular structure can be coupled with the second ring by the receiving portions receiving the plurality of fasteners.

The first ring can be aligned with the second ring such that the lumen of the first tubular structure and the lumen of the second tubular structure are aligned in fluid communication with one another. The first ring can be coupled with the second ring to join the first tubular structure with the second tubular structure, providing a continuous passage between the first tubular structure and the second tubular structure. In at least one example, a cap can be positioned about the first and the second ring to ensure the connection between the first ring and the second ring.

Figure 17A:
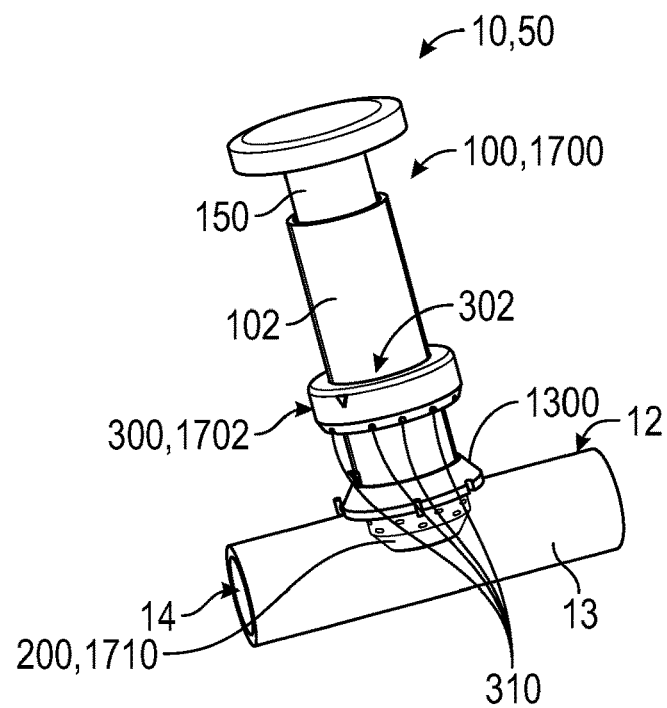
FIG. 17A illustrates a fixation device engaging with a side hole of a tubular structure.

FIGS. 17A-17E illustrate examples of an anastomotic coupler 10 which is operable to couple an end of a tubular structure 12 with a side of a tubular structure 12. Elements described in the system of FIGS. 17A-18 that have similar or the same name and/or the same reference numbers as elements in the disclosure for FIGS. 1-16 may have the same features as discussed above. While the discussion below for FIGS. 17A-17E may highlight some differences in features, the disclosure for the system of FIGS. 17A-18 are not limited to those and may also include any and/or all of the features as discussed above.

FIG. 17A illustrates alignment and positioning of a fixation device 100 and a ring 300 on a tubular structure 12. The fixation device 100 and the ring 300 are positioned such that the ring 300 can be coupled to the tubular structure 12 where an aperture 302 of the ring 300 can be aligned with a hole 1300 formed in a wall 13 of the tubular structure 12. In other words, the tubular structure 12 has a hole 1300 formed in a side wall 13. In at least one example, a cutting mechanism (not shown) can be operable to cut the hole 1300 in the wall 13 of the tubular structure 12. In some examples, the cutting mechanism can be a separate component operable to cut a precise hole 1300 in the wall 13 of the tubular structure 12. In some examples, the cutting mechanism can be part of the fixation device 1700 such that only one component is needed in the fixation device 1700 to cut a hole 1300 and couple the ring 300 to the tubular structure 12. The cutting mechanism can create a symmetrical, controllable-sized opening in the side wall 13 of the tubular structure 12.

In at least one example, the fixation device 1700 can be similar to fixation device 100 as discussed herein. In some examples, fixation device 1700 may be modified to couple the ring 1702 to the wall 13 of the tubular structure 12 to align with the hole 1300 in the wall 13 instead of coupling the ring 1702 to the tubular structure 12 in line with the lumen 14 of the tubular structure. In at least one example, the fixation device 1700 can include a stop which extends radially from the housing 102 such that the wall 13 of the tubular structure 12 abuts the stop. Accordingly, the fixation device 1700 provides guidance to the user for when the fixation device 1700 is in a desired position. In some examples, the stop can include a plurality of alignment components corresponding with alignment components of the ring 1702. As such, when the ring 1702 is aligned, the alignment components of the stop are aligned with the alignment components of the ring 1702.

Figure 17B:
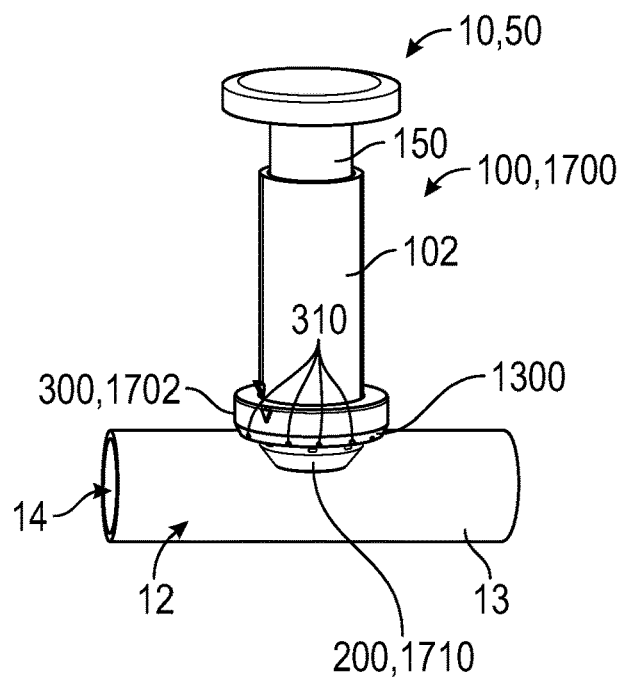
FIG. 17B illustrates a ring being aligned on the tubular structure of FIG. 17A.

As illustrated in FIGS. 17A and 17B, a cartridge 1710 can be disposed within the lumen 14 of the tubular structure 12. The cartridge 1710, similar to cartridge 300, includes a plurality of fasteners 260 (for example shown in 17C-17E) operable to be received in corresponding plurality of receiving portions 310 in the ring 300. The ring 1702, as illustrated in FIGS. 17A-17E has a cylindrical shape. However, in other examples, the ring 1702 can have any suitable shape such that the ring 1702 can be aligned with the hole 1300 and prevent leakage between the tubular structure 12 and the ring 1702. The ring 1702, in some examples, may include a sealing component operable to abut against the wall 13 of the tubular structure 12 to prevent leakage of fluid.

In some examples, the position of the receiving portions 310 in the ring 1702 may be adjusted to better receive the plurality of fasteners 260 and provide a stronger coupling between the ring 1702 and the tubular structure 12. For example, as illustrated in FIGS. 17A-17E, the receiving portions 310 may be disposed towards the bottom of the ring 1702 so that the receiving portions 310 are adjacent to the tubular structure 12.

Similarly, in some examples, the position of the fasteners 260 in the cartridge 1710 may be adjusted towards the top to be adjacent to the wall 13 of the tubular structure 12. Accordingly, the distance between the fasteners 260 in the cartridge 1710 and the receiving portions 310 can be smaller to minimize the chance of error in coupling the ring 1702 with the tubular structure 12.

Figure 17C:
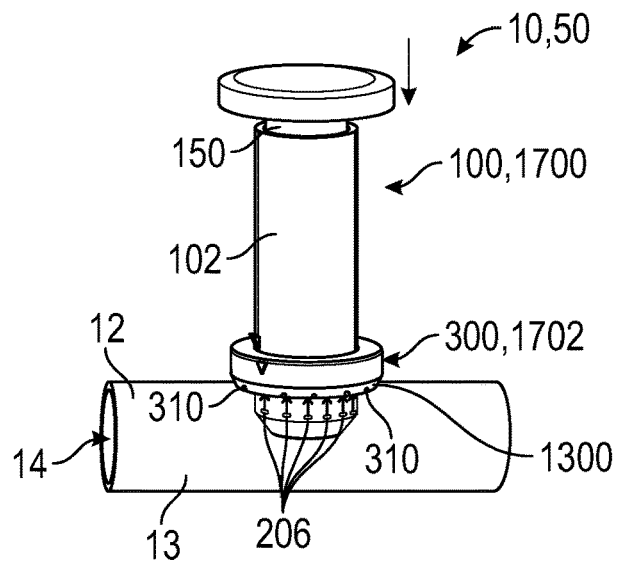
FIG. 17C illustrates actuation of the fixation device.
Figure 18:
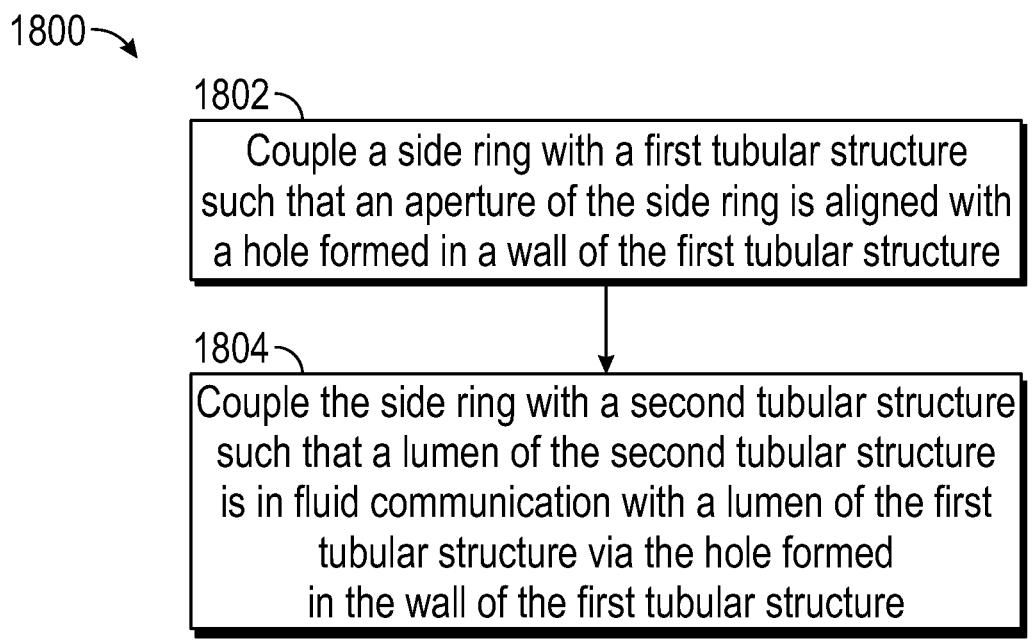
FIG. 18 is a flow chart of a method for coupling an end of a tubular structure with a side of a tubular structure.

As illustrated in FIG. 17A-17C, the ring 1702 can be positioned opposite the cartridge 1710 in relation to the wall 13 of the tubular structure 12. The ring 1702 can be positioned external of the tubular structure 12 so that the ring 1702 does not cause any obstruction in the lumen 14 of the tubular structure 12. The cartridge 1710, as illustrated in FIGS. 17A-17C, can be positioned inside the lumen 14 of the tubular structure 12 to push the fasteners 260 across the wall 13 of the tubular structure 12 into the receiving portions 310 of the ring 1702. In some examples, the cartridge 1710 may also be positioned external of the tubular structure 12, so long as the fasteners 260 can couple the ring 1702 with the tubular structure 12.

As illustrated in FIG. 17C, the fixation device 1700 can be actuated so that the plurality of fasteners 260 puncture the tubular structure 12 and are received by the receiving portions 310. Accordingly, the tubular structure 12 can be coupled with the ring 1702. In at least one example, as illustrated in FIG. 17C, the fixation device 1700 can include a pusher rod 150. Upon actuation of the fixation device 1700, the pusher rod 150 can translate along a longitudinal axis to activate drivers to push the corresponding fasteners 260 from the cartridge 1710. In some examples, the fixation device 1700 can have any suitable mechanism to activate the drivers to push the fasteners 260 from the cartridge 1710.

Figure 17D:
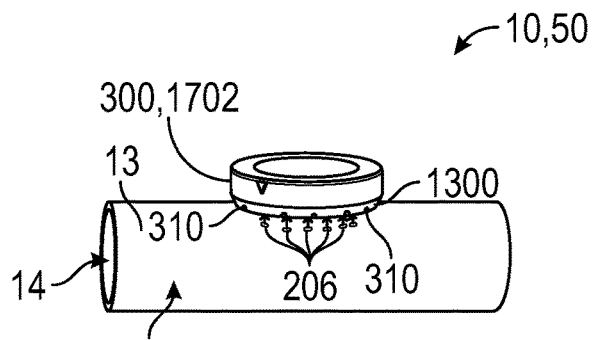
FIG. 17D illustrates the ring being coupled with the side of the tubular structure.

As illustrated in FIG. 17D, after the ring 1702 is coupled with the tubular structure 12, the fixation device 1700, along with the cartridge 1710, can be removed. The ring 1702 remains coupled with the tubular structure 12 such that the aperture 302 of the ring 1702 is aligned with the hole 1300 in the wall 13 of the tubular structure 12.

Figure 17E:
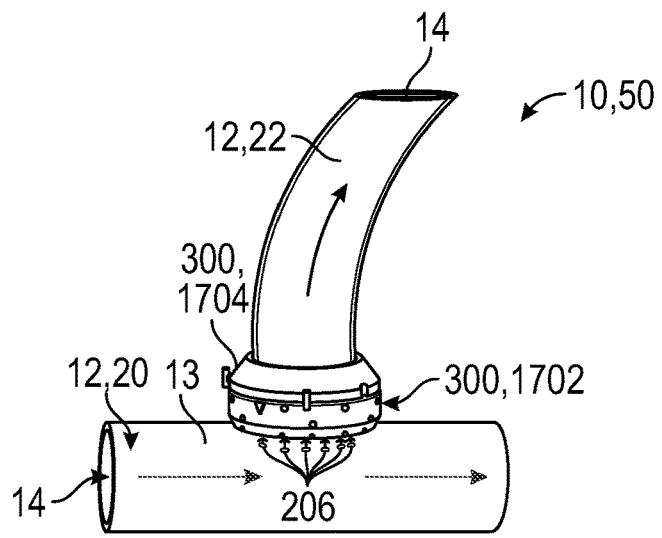
FIG. 17E illustrates a second tubular structure being coupled with the tubular structure.

As illustrated in FIG. 17E, the ring 1702 is operable to be coupled with a second tubular structure 22 such that a lumen 14 of the second tubular structure 22 is in fluid communication with the lumen 14 of the tubular structure 20 via the hole 1300 formed in the wall 13 of the tubular structure 20. The side ring 1702 is operable to be coupled with the first tubular structure 20 such that the aperture 302 of the side ring 1702 is aligned with the hole 1300 formed in the wall 13 of the first tubular structure 12. The end ring 1704, similar to the rings 350, 360 as illustrated in FIGS. 1-14, is operable to be coupled with a second tubular structure 22 such that the aperture 302 of the end ring 1704 is in line with the lumen 14 of the second tubular structure 22. The side ring 1702 is operable to be coupled with the end ring 1704 such that the lumen 14 of the second tubular structure 22 is in fluid communication with the lumen 14 of the first tubular structure 20 via the hole 1300 formed in the wall 13 of the first tubular structure 20. Accordingly, an end-to-side anastomosis is achieved. In some examples, the side ring 1702 and the end ring 1704 create a seal to prevent fluid leakage. The seal can be achieved by any suitable mechanism.

As illustrated in FIG. 17E, fluid may flow through the lumen 14 of the first tubular structure 20 while some fluid may flow into and through the lumen 14 of the second tubular structure 22. In some examples, fluid from the second tubular structure 22 may flow into the first tubular structure 20.

The aforementioned side-to-end anastomotic coupler 50 and system provides users with a better, more reliable alternative to the conventional techniques. The only technique conventionally practiced for side-to-end anastomosis is through hand-sewn suture techniques. Hand-sewn suture techniques are labor intensive and prone to failure. Similarly, the process of creating the side opening in the tubular structure is conventionally completed in an uncontrolled fashion using a scalpel or scissors to haphazardly cut the side of the structure, which can result in an asymmetric opening of variable size.

Referring to FIG. 18, a flowchart is presented in accordance with an example embodiment. The method 1800 is provided by way of example, as there are a variety of ways to carry out the method. The method 1800 described below can be carried out using the configurations illustrated in FIG. 1-17E, for example, and various elements of these figures are referenced in explaining example method 1800. Each block shown in FIG. 18 represents one or more processes, methods or subroutines, carried out in the example method 1800. Furthermore, the illustrated order of blocks is illustrative only and the order of the blocks can change according to the present disclosure. Additional blocks may be added or fewer blocks may be utilized, without departing from this disclosure. The example method 1800 can begin at block 1802.

At block 1802, a side ring is coupled with a first tubular structure such that an aperture of the side ring is aligned with a hole formed in a wall of the first tubular structure.

At block 1804, the side ring is coupled with a second tubular structure such that a lumen of the second tubular structure is in fluid communication with a lumen of the first tubular structure via the hole formed in the wall of the first tubular structure. In at least one example, the second tubular structure can be coupled with an end ring such that an aperture of the end ring is in line with the lumen of the second tubular structure. The side ring can be coupled with the end ring to join the first tubular structure with the second tubular structure. In at least one example, the side ring and the end ring can create a seal to prevent fluid leakage.

The disclosures shown and described above are only examples. Even though numerous properties and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

The invention claimed is:

1. An anastomotic coupler comprising:
   a ring;
   a cartridge including a plurality of fasteners,
   wherein the ring is aligned with the cartridge in that the cartridge is disposed within a lumen of a tubular structure and the ring is positioned external of the tubular structure,
   wherein the plurality of fasteners are operable to puncture the tubular structure and be received by the ring such that the tubular structure is coupled with the ring, wherein the ring is operable to be coupled with a second tubular structure such that a lumen of the second tubular structure is in fluid communication with the lumen of the tubular structure via a hole formed in a wall of the tubular structure.

2. The anastomotic coupler of claim 1, wherein the ring forms an aperture that aligns with the hole formed in the wall of the tubular structure.

3. The anastomotic coupler of claim 1, wherein a fixation device includes a stop, the stop extending radially from a housing such that the wall of the tubular structure abuts the stop.

4. The anastomotic coupler of claim 3, wherein the stop includes a plurality of alignment components corresponding with alignment components of the ring, wherein when the ring is aligned, the alignment components of the stop are aligned with the alignment components of the ring.

5. The anastomotic coupler of claim 1, wherein the cartridge includes a plurality of drivers corresponding with the plurality of fasteners, wherein upon actuation of a fixation device, the drivers activate to push the corresponding fasteners from the cartridge.

6. The anastomotic coupler of claim 5, wherein the fixation device includes a pusher rod, wherein upon actuation of the fixation device, the pusher rod translates along a longitudinal axis to activate the drivers.

7. The anastomotic coupler of claim 1, wherein the plurality of fasteners include stents, tacks, staples, pins, adhesive, internal ring, internal mesh, wire, clamp, coil, and/or suture.

8. A system comprising:
   a side ring forming an aperture, the side ring operable to be coupled with a first tubular structure such that the aperture of the side ring is aligned with a hole formed in a wall of the first tubular structure;
   an end ring forming an aperture, the end ring operable to be coupled with a second tubular structure such that the aperture of the end ring is in line with a lumen of the second tubular structure,
   wherein the side ring is operable to be coupled with the end ring such that the lumen of the second tubular structure is in fluid communication with a lumen of the first tubular structure via the hole formed in the wall of the first tubular structure; and
   a cartridge including a plurality of fasteners,
   wherein the side ring is aligned with the cartridge in that the cartridge is disposed within the lumen of the first tubular structure and the side ring is positioned external of the first tubular structure, wherein the plurality of fasteners are operable to puncture the first tubular structure and be received by the side ring such that the first tubular structure is coupled with the side ring.

9. The system of claim 8, wherein the side ring and the end ring create a seal to prevent fluid leakage.

10. The system of claim 8, further comprising a fixation device wherein the cartridge includes a plurality of drivers corresponding with the plurality of fasteners, wherein upon actuation of the fixation device, the drivers activate to push the plurality of fasteners from the cartridge into a plurality of receiving portions of the side ring to couple the first tubular structure with the side ring.

11. The system of claim 10, wherein the fixation device includes a pusher rod, wherein upon actuation of the fixation device, the pusher rod translates along a longitudinal axis to activate the drivers.

12. The system of claim 11, wherein the pusher rod is tapered from a front portion with a smaller diameter to rear portion with a larger diameter.

13. The system of claim 8, wherein the plurality of fasteners include stents, tacks, staples, pins, adhesive, internal ring, internal mesh, wire, clamp, coil, and/or suture.

14. The system of claim 8, further comprising a cutting mechanism operable to cut the hole in the wall of the first tubular structure.

* * * * *